United States Patent
Yoo et al.

(10) Patent No.: US 8,939,769 B2
(45) Date of Patent: Jan. 27, 2015

(54) MULTI-SENSORY MANIPULATION

(75) Inventors: Herb Yoo, Beaverton, OR (US); Alan W. Reichow, Beaverton, OR (US)

(73) Assignee: NIKE, Inc., Beaverton, OR (US)

( * ) Notice: Subject to any disclaimer, the term of this patent is extended or adjusted under 35 U.S.C. 154(b) by 344 days.

(21) Appl. No.: 13/180,020

(22) Filed: Jul. 11, 2011

(65) Prior Publication Data
US 2013/0017520 A1    Jan. 17, 2013

(51) Int. Cl.
*H04R 25/00*    (2006.01)
(52) U.S. Cl.
CPC .................................. *H04R 25/606* (2013.01)
USPC ....................................................... 434/247
(58) Field of Classification Search
CPC .................................................. G09B 19/0038
USPC .................. 434/247; 351/159.01, 159.6, 151; 381/71.1, 91, 92, 94.7; 455/550.1
See application file for complete search history.

(56) References Cited

U.S. PATENT DOCUMENTS

| | | | |
|---|---|---|---|
| 6,176,576 | B1 | 1/2001 | Green et al. |
| 7,213,917 | B2 | 5/2007 | Jannard et al. |
| 7,760,898 | B2 | 7/2010 | Howell et al. |
| 8,379,870 | B2 * | 2/2013 | Nicolino et al. ............... 381/56 |
| 2003/0068057 | A1 | 4/2003 | Miller et al. |
| 2007/0237339 | A1 * | 10/2007 | Konchitsky ..................... 381/91 |
| 2008/0055541 | A1 | 3/2008 | Coulter et al. |
| 2009/0086988 | A1 | 4/2009 | Ou et al. |
| 2009/0216070 | A1 | 8/2009 | Hunt et al. |
| 2011/0032476 | A1 * | 2/2011 | Brown et al. ................. 351/169 |

OTHER PUBLICATIONS

Notification of Transmittal of the International Search Report and the Written Opinion of the International Searching Authority, or the Declaration dated Sep. 28, 2012, 12 pages.

* cited by examiner

*Primary Examiner* — Robert J Utama
*Assistant Examiner* — Elroy S Crocker
(74) *Attorney, Agent, or Firm* — Shook, Hardy & Bacon L.L.P.

(57) ABSTRACT

Aspects of the present invention relate to a multi-sensory manipulation system. The multi-sensory manipulation system is useable to train one or more senses through the manipulation of one or more sensory inputs as perceived by a user. The multi-sensory system may be used train a variety of senses, such as vision, hearing, olfactory, taste, touch, and the like. Consequently, the multi-sensory system may be comprised of a first sensory vitiation device that vitiates a sensory input for the first sense. The multi-sensory system may be comprised of a first sensory vitiation driver that generates vitiations instructions useable by the first sensory vitiation device. The multi-sensory system may also be comprised of a controller to coordinate one or more sensory drivers and/or one or more sensory vitiation devices to allow for the training of one or more senses through the manipulation of multiple sensory inputs.

20 Claims, 7 Drawing Sheets

MULTI-SENSORY MANIPULATION

BACKGROUND

Athletic achievement in both individual and team sports continues to improve. Scientifically proven nutrition and training regimes are available to athletes at all levels from personal trainers, specialized coaches, and Internet-based trainers and training programs. In addition, athletic equipment, footwear, and apparel have been developed to offer athletes superior performance as well as a stylish appearance and comfort. Injury treatment has also improved, and some serious injuries that were previously career ending can be treated with techniques that permit nearly complete recovery with only a brief period of rehabilitation. Thus, athletes are fitter, stronger, better trained, better equipped, and better cared for than ever before.

While athletic performance is a direct function of an athlete's physical condition, many sports demand that the athlete accurately perceive and respond to the position and motion (such as velocity, acceleration, deceleration) of teammates, competitors, and sport-specific objects such as footballs, basketballs, baseballs, pucks, or other objects. For example, successful baseball batters or football quarterbacks appear to have superior visual skills, at least with respect to situations encountered in their sports. In order to increase personal performance, athletes have become interested in sensory training as another avenue toward enhanced performance. For example, hitters want to improve their vision so as to be able to see the seams on a 90+ mph fastball or read a pitch type (e.g., ball rotation detection). Thus, athletes are targeting achieving superior visual dexterity to complement their physical dexterity. Unfortunately, available methods for sensory training and assessment are generally not well tailored to the specific skills needed for a selected sport/position, nor are the methods readily configurable to provide the varied training that can be required. Accordingly, improved methods and apparatus are needed for sensory training.

SUMMARY

Aspects of the present invention relate to a multi-sensory manipulation system. The multi-sensory manipulation system is useable to train one or more senses through the manipulation of one or more sensory inputs as perceived by a user. The multi-sensory system may be used to train a variety of senses, such as vision, hearing, smell, taste, touch, and the like. Consequently, the multi-sensory system may be comprised of a first sensory vitiation device that vitiates a sensory input for the first sense. The multi-sensory system may be comprised of a first sensory vitiation driver that generates vitiations instructions useable by the first sensory vitiation device. The multi-sensory system may also be comprised of a controller to coordinate one or more sensory drivers and/or one or more sensory vitiation devices to allow for the training of one or more senses through the manipulation of multiple sensory inputs.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE SEVERAL VIEWS OF THE DRAWINGS

Illustrative aspects of the present invention are described in detail below with reference to the attached drawing figures, which are incorporated by reference herein and wherein.

DETAILED DESCRIPTION

Figure 1:
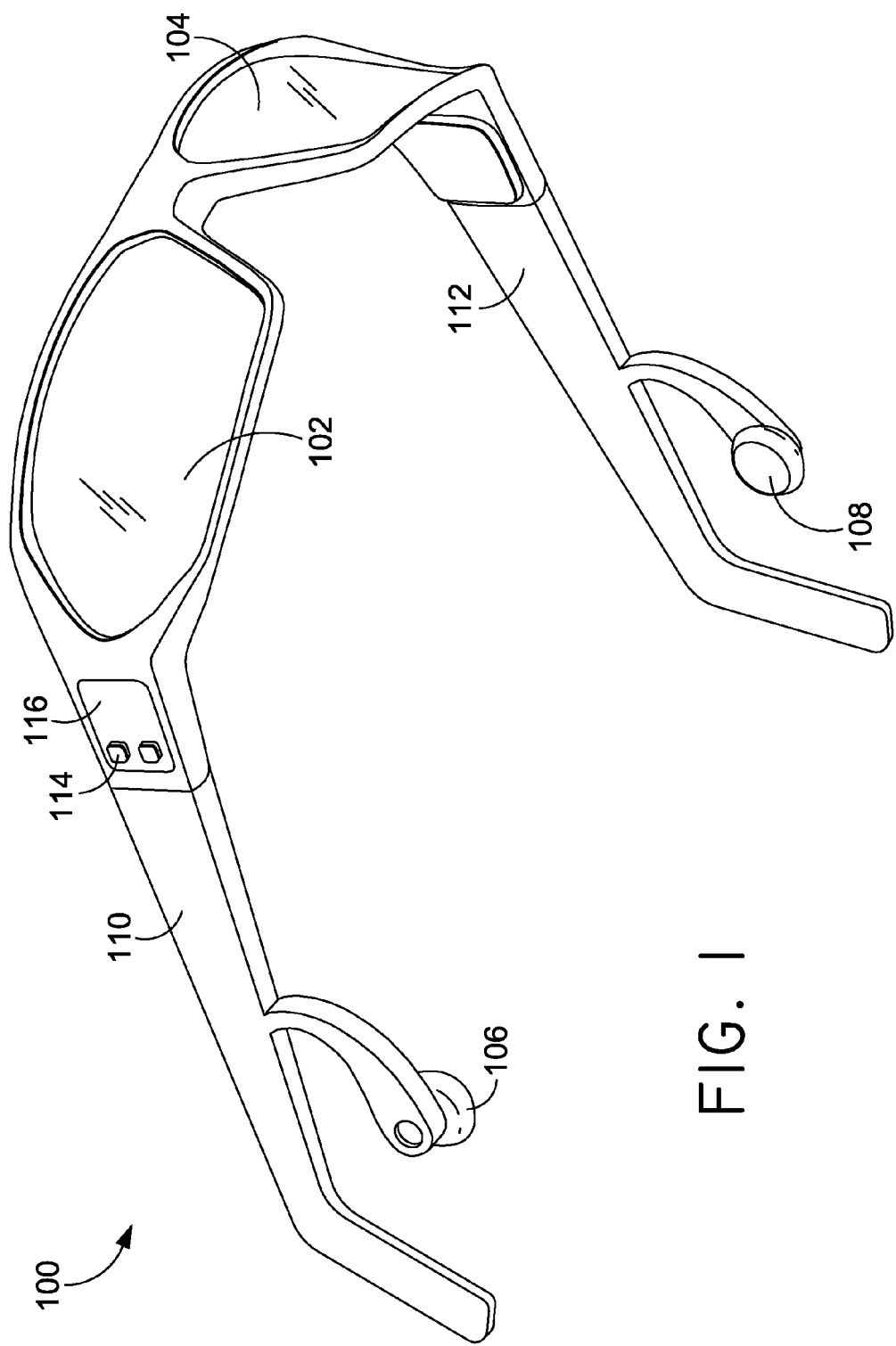
FIG. 1 illustrates a representative example of a multi-sensory training system, in accordance with aspects of the present invention.

The subject matter of aspects of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

Aspects of the present invention relate to a multi-sensory manipulation system. The multi-sensory manipulation system is useable to train one or more senses through the manipulation of one or more sensory inputs as perceived by a user. The multi-sensory system may be used to train a variety of senses, such as vision, hearing, olfactory, taste, touch, and the like. Consequently, the multi-sensory system may be comprised of a first sensory vitiation device that vitiates a sensory input for the first sense. The multi-sensory system may be comprised of a first sensory vitiation driver that generates vitiations instructions useable by the first sensory vitiation device. The multi-sensory system may also be comprised of a controller to coordinate one or more sensory drivers and/or one or more sensory vitiation devices to allow for the training of one or more senses through the manipulation of multiple sensory inputs.

Accordingly, in one aspect, the present invention provides a sensory manipulation system. The sensory manipulation system is comprised of an audio vitiation device. The sensory manipulation system may also be comprised of an audio vitiation driver that generates audio information for output by the audio output device, which consequently cycles from a first audio state to a second audio state. The first audio state vitiates environmental noise more than the second audio state. The sensory manipulation system may also be comprised of an audio vitiation controller that, in response to a sensory manipulation-level input, controls a duty cycle, a duration, and/or a frequency of the first audio state or the second audio state.

In another aspect, the present invention provides a sensory manipulation system. The sensory manipulation system may be comprised of an eyewear configured with electrically variable spectral transmittance. Additionally, the sensory manipulation system may be comprised of an audio vitiation device configured to cycle through two or more states of a variable audio transmittance. The sensory manipulation system may also be comprised of a controller configured to control the eyewear and the audio vitiation device such that the electrically variable spectral transmittance of the eyewear and the variable audio state of the audio vitiation device are adjustable in response to a user input.

A third aspect of the present invention provides another exemplary sensory manipulation system. The sensory manipulation system may be comprised of eyewear configured with electrically variable spectral transmittance that cycles between a first visual state and a second visual state. The first visual state obscures more than the second visual state. The sensory manipulation system also is comprised of an audio vitiation device configured to cycle a variable audio transmittance between a first audio state and a second audio state. The first audio state vitiates more than the second audio state. The sensory manipulation system may also be comprised of a controller configured to control the eyewear and the audio vitiation device such that the first visual state and the first audio state are controlled contemporaneously.

Having briefly described an overview of aspects of the present invention, an exemplary operating environment suitable for implementing aspects hereof is described below.

As used herein, the singular forms "a," "an," and "the" include the plural forms unless the context clearly dictates otherwise. Additionally, the term "includes" means "comprises." The described systems, apparatus, and methods should not be construed as limiting in any way. Instead, the present disclosure is directed toward all novel and nonobvious features and aspects of the various disclosed aspects, alone and in various combinations and sub-combinations with one another. The disclosed systems, methods, and apparatus are not limited to any specific aspect or feature or combination thereof, nor do the disclosed systems, methods, and apparatus require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show all the various ways in which the disclosed systems, methods, and apparatus can be used in conjunction with other systems, methods, and apparatus.

FIG. 1 depicts an exemplary sensory manipulation system 100 in accordance with aspect of the present invention. The sensory manipulation system 100 allows for the manipulation of one or more sensory inputs perceived by a user. For example, a human participating in a sensory demanding field (e.g. doctors, mechanics, athletes, etc.) may benefit from training one or more senses to enhance that sense or other senses. Senses that are contemplated as being manipulated by a sensory manipulation system include, but are not limited to, visual, audible, tactile, balance, olfactory, taste, pain, direction, and the like. Therefore, it is contemplated that two or more of the senses relied upon by a user may be manipulated to train those senses (or other senses) to the potential benefit of the user.

As will be discussed in more detail hereinafter, it is contemplated that a variety of multi-sensory manipulation techniques may be implemented. A first multi-sensory training technique may include blocking one or more senses while training one or more other senses. A second multi-sensory training technique may include sensory isolation. Sensory isolation may focus on one or more senses while adding stimuli to one or more other senses. Further, it is contemplated that sensory isolation may focus on one or more senses while inhibiting stimuli to one or more other senses. A third multi-sensory training technique may include staggering sensory input manipulation between two or more groups (where a sensory group may consist of a single sense or multiple senses). Further, it is contemplated that directional sensory manipulation may also be incorporated into a multi-sensory training technique. A directional sensory manipulation may include manipulating sensory input to a first sensory receiver/receptor (e.g., left ear, left eye), while providing a different (or similar) sensory manipulation to an alternative related sensory receiver/receptor (e.g., right ear, right eye). It is contemplated that any combination of multi-sensory training techniques may be implemented in any order/sequence/duration within the scope contemplated to provide sensory isolation, integration, filtration, selection, and/or the like.

The sensory manipulation system 100, in this exemplary aspect, manipulates a user's sense of vision and the user's sense of hearing. To accomplish a sensory manipulation, a traditional input is altered. For example, a visual input (e.g., light waves) may be altered prior to being perceived by the user. An exemplary system for manipulating visual senses utilizing a variable spectral transmittance lens is discussed in a co-pending U.S. non-provisional patent application having an application Ser. No. 13/009,417, entitled Adjustable Spectral Transmittance Eyewear, filed Jan. 19, 2011, which is expressly incorporated by reference herein in its entirety. The variable spectral transmittance lenses ("strobe glasses") may strobe from a first spectral transmittance state to a second spectral transmittance state to interfere with visual input as perceived by the user. For example, it is contemplated that a user of the strobe glasses may have the glasses cycle between the first state (e.g., substantially transparent) and the second state (e.g., substantially obscuring) while performing an athletic exercise (e.g., catching a ball). Strobing from a substantially transparent state to a substantially obscuring state reduces the amount of visual input perceived by the user during a given time frame. As a result, the user is trained to perform actions, make decisions, or react, with less information. Consequently, when the user is performing an activity that is not affected by a strobing cycle, the user may react better/faster with more complete information.

The concept of "training" a sense expands from those examples provided above with the visual sense. Similarly, it is contemplated that inputs for other senses (e.g., smells for olfactory senses, sounds for audible senses, feelings for tactile senses, etc.) may also be manipulated to selectively reduce (or increase in some aspects) those inputs to train the user to perform with less information than is typically provided. Therefore, when a traditional quantity of the sensory input is provided (e.g., in an actual competition environment), the user that was trained to perform with less input is able to reduce a reaction, decision, and/or response time because less sensory input is needed for that user.

Extrapolating this concept further, as is contemplated herein, two or more senses may be manipulated concurrently in a defined manner to further train one or more of the senses. For example, a user may compensate for a reduction in a first type of sensory input by relying more heavily than normal on a secondary sensory input. For example, when visual input is reduced, a user may enhance their audible perception to compensate for the reduction in visual input.

An exemplary scenario where training of multi-senses may be realized as advantageous includes a defensive lineman playing American football. Traditionally, a quarterback controls the snap of a football from a offensive center through the use of an audible snap count. The audible snap count allows other members of the offensive team to anticipate and be aware of the ball movement by the center without requiring their visual inspection to confirm movement. Just as the offensive team is able to use the audible count to know when the ball may move, the defensive team may also anticipate ball movement from the quarterback's snap count. To reduce a defensive advantage from the audible snap count, offensive teams may alter the snap count to provide false information during the snap count. As a result, it is advantageous for the defensive team, including the defensive lineman, to ignore the audible sensory information in favor of visual information of the ball moving. Consequently, it is contemplated that a defensive lineman may realize an advantage through training of audible and visual sensory manipulation to teach/learn to ignore audible information (which may be intentionally conflicting) in favor of visual information. This is but one exemplary scenario in which advantages of multi-sensory manipulation may be realized.

Returning to FIG. 1, the sensory manipulation system 100 contemplated manipulates at least a visual input and an audible input as perceived by a user. For example, it is contemplated that electrically variable spectral transmittance of a lens 102 and a lens 104 may obscure light waves passing through each of the lenses such that a user may not be able to accurately perceive an object obscured by the lenses. Varying the spectral transmittance of a lens may obscure objects perceived by a user by scattering light, distorting light, blocking light, diffusing light, altering a percentage of transmitted light, or other techniques that reduce a user's ability to recognize an object as seen through the lens 102 and/or the lens 104. Therefore, the term "spectral transmittance" is used herein to describe altering a perceived state of light as transmitted by a material. Further, it is contemplated that one or more lenses of the sensory manipulation system are curved. For example, the lens 102 and/or 104 may be curved in a left-right and/or top-down manner to, among other benefits, provide sensory input manipulation at greater extremes of a field of view for a user.

In one example, it is contemplated that the lens 102 and the lens 104 utilize a liquid crystal technology to obscure an object as perceived through the lens by a user. For example, it is contemplated that a polymer dispersed liquid crystals, nematic liquid crystals, cholestric liquid crystals, and/or other electrically switchable optical materials (e.g., twisted nematic, in-plane switching, advanced fringe field switching, vertical alignment, and blue phase mode) may be utilized to manipulate visual input.

It is contemplated that a sensory manipulation system may include a single lens that affects light perceived through both eyes of a typical user. However, it is contemplated that the single lens may have two or more zones. For example, a first zone may primary affect light perceived by a first eye of a user and a second zone may primarily affect light as perceived by a second eye of the user. Each zone may be activated independently of one another. Similarly, two or more zones may be activated concurrently with one another. As will be discussed hereinafter, a controller and/or may control a frequency, duty cycle, duration, and/or coordination of spectral transmittance of one or more of the potential zones.

The lenses 102 and 104 may be secured in a frame having a first temple 110 and a second temple 112, which is traditional in eyewear. However, the temples 110 and 112 may include one or more additional components to be discussed hereinafter. For example, the frame in general, or the temples 110 and 112 in particular, may be coupled with a memory, a processor, a controller, a use input interface 114, a level selection output display 116, a power source, a microphone, an audio vitiation driver, an audio output device, and the like.

The sensory manipulation system 100 is comprised of a first earbud 106 and a second earbud 108. An earphone is an example of an audio vitiation device capable of vitiating environmental noise. For example, an audio vitiation device may either be a passive device (e.g., blocking sound waves to reduce their perceived power) or an active device (e.g., utilizing a speaker to produce a distracting noise or an anti-phase noise). The term vitiation, as used herein, means to reduce the perceptive value of an input and/or to impair the quality of the input. For example, the vitiation of perceivable audio is the reduction of audible input (e.g., environmental noise traditionally used as a sensory input). Environmental noise is sound energy that is typically perceived by a typical person. In an real world example, an athlete may rely on audible information to supplement visual information that is not available (e.g., a runner may not be able to see an opponent that is behind the runner, but utilizing audible inputs, the runner may know the opponent is behind the runner).

An exemplary earbud is sizeable to be inserted into a portion of the ear (e.g., external auditory canal) to focus audio input produced by an audio output device (e.g., speaker) and/or to obstruct ambient noise from entering the auditory canal. It is also contemplated that an earbud is external to the ear and is positionable adjacent to the pinna (i.e., outer flap of tissue) of an ear. Audio vitiation devices are contemplated as being coupled directly to one or more portions of the eyewear. Additionally, it is contemplated that the audio vitiation devices may be directly coupled to a portion of the first temple 110 and/or the second temple 112. Therefore, it is contemplated that an earbud positioning member extends from a portion of the eyewear to aid in maintaining a position of the earbud that is relative to a user. This positioning member may be rigid or flexible in nature.

Regardless if the audio vitiation device is external fitting or internal fitting, it is contemplated that the audio vitiation device may be either passive or active. A passive audio vitiation device may merely obstruct the transmission of audio input provided by the environment. For example, a passive audio vitiation device may be selectably obstructing sound waves. In a first position, the passive audio vitiation device may inhibit a user from clearly hearing an environmental noise. In a second position, the passive vitiation device may allow the passive audio vitiation device to transmit audio input from the environment to the user's ear. An example of a passive audio vitiation device in the first state may be protection ear wear used by musicians, hunters, construction workers, and other high-decibel environment workers.

An active audio vitiation device is one that adds additional audio input to vitiate environmental noise. For example, the insertion of an anti-phased sound wave into a sound profile effectively "cancels" out at least a portion of the environmental noise that would be interpretable otherwise. Anti-phased sound waves, sometimes referred to an active noise reduction ("ANR"), are a sound wave with similar amplitude to environmental noise but with inverted phase (also known as antiphase) to the original sound. The waves (i.e., environmental and anti-phased) combine to form a new wave, in a process called interference, and effectively cancel each other out—an effect which is called phase cancellation. Depending on the circumstances and the method used, the resulting sound wave may be so faint as to be inaudible to human ears.

A passive audio vitiation device may operate with an adjustable opening that, when in a closed position, vitiates audible input more than when in an open or partly open position. The opening may be adjusted utilizing mechanical and/or electrical processes. For example, much like a camera shutter may operate electrically or mechanically to open and close, the audio vitiation device may similarly function. Additionally, it is contemplated that the audio vitiation device is not limited to a binary first state and second sate. Instead, a plurality of states may be incorporated to provide an adjustable level of vitiation to an audible input. Additional examples of mechanisms for changing a level of audio vitiation of a passive audio vitiation device include one or more valves that mechanically or electronically open to allow sound waves to pass, one or more adjustable mufflers may be utilized, and/or the like. Further, it is contemplated that one or more of the electronic or mechanical audio vitiation techniques may be utilized concurrently to achieve exemplary aspects.

An active audio vitiation device may operate in a number of configurations. For example, the active audio vitiation device may be located adjacent to a user (e.g., earbuds) and/or removed from the user (e.g., closer to a source of at least a portion of the environmental noise). Further, it is contemplated that the audio active vitiation device utilizes sound waves corresponding to at least a portion of the environmental noise to be vitiated (e.g., anti-phased noise). Further it is contemplated that an active audio noise vitiation device may utilize a Gaussian distribution of noise (e.g., white noise) that is not specifically adjusted to a real-time environmental noise. Further yet, it is contemplated that an active audio noise vitiation device may also (or in the alternative) utilize a set sound wave (e.g., predetermined pitch, tone, decibel, and/or the like) to produce a distracting audio sound.

Regardless of the technique utilized in an active audio vitiation device, the device may be comprised of an audio output device to produce the "active" portion. For example, a speaker may be employed by an active audio vitiation device to produce a desired sound wave (e.g., anti-phased, Gaussian, predefined). Additionally, it is contemplated that the first earbud 106 and/or the second earbud 108 may produce one or more sounds from a digital file, such as an MP3 file. Consequently, it is also contemplated that the sensory manipulation device 100 is comprised of one or more audio file playing components that allow for a stored or received audio file to be converted into a sound wave that is able to be perceived by an exemplary user. Additional examples of an audio file include real-time or near real-time communications from one or more sources (e.g., one-way/two-way radio communications). For example, it is contemplated that the earbuds 106 and/or 108 may produce a sound that reflect audio commands (e.g., voice, code) that are useable by a wearer when training one or more additional senses (or even an auditory sense).

Additional components of an exemplary sensory manipulation system will be discussed hereinafter with respect to FIG. 4.

Returning to FIG. 1, the sensory manipulation system 100 depicted in FIG. 1, provides the earbuds 106 and 108. In this example, the earbuds (i.e., audio vitiation device) are directly coupled to respective temples of the eyewear frame resulting in a unified training device. However, it is contemplated (as depicted in FIG. 2) that components for training different senses may, in the alternative, be independent from one another.

Advantages may be recognized by incorporating at least two sensory manipulation devices into a common form factor, as is depicted in FIG. 1. For example, a controller (to be discussed hereinafter) may be utilized to coordinate the concurrent use of multiple sensory manipulation devices. Additionally, a common power source, processor, and/or memory may be utilized when two or more sensory manipulation devices share at least a portion of a common apparatus.

Figure 2:
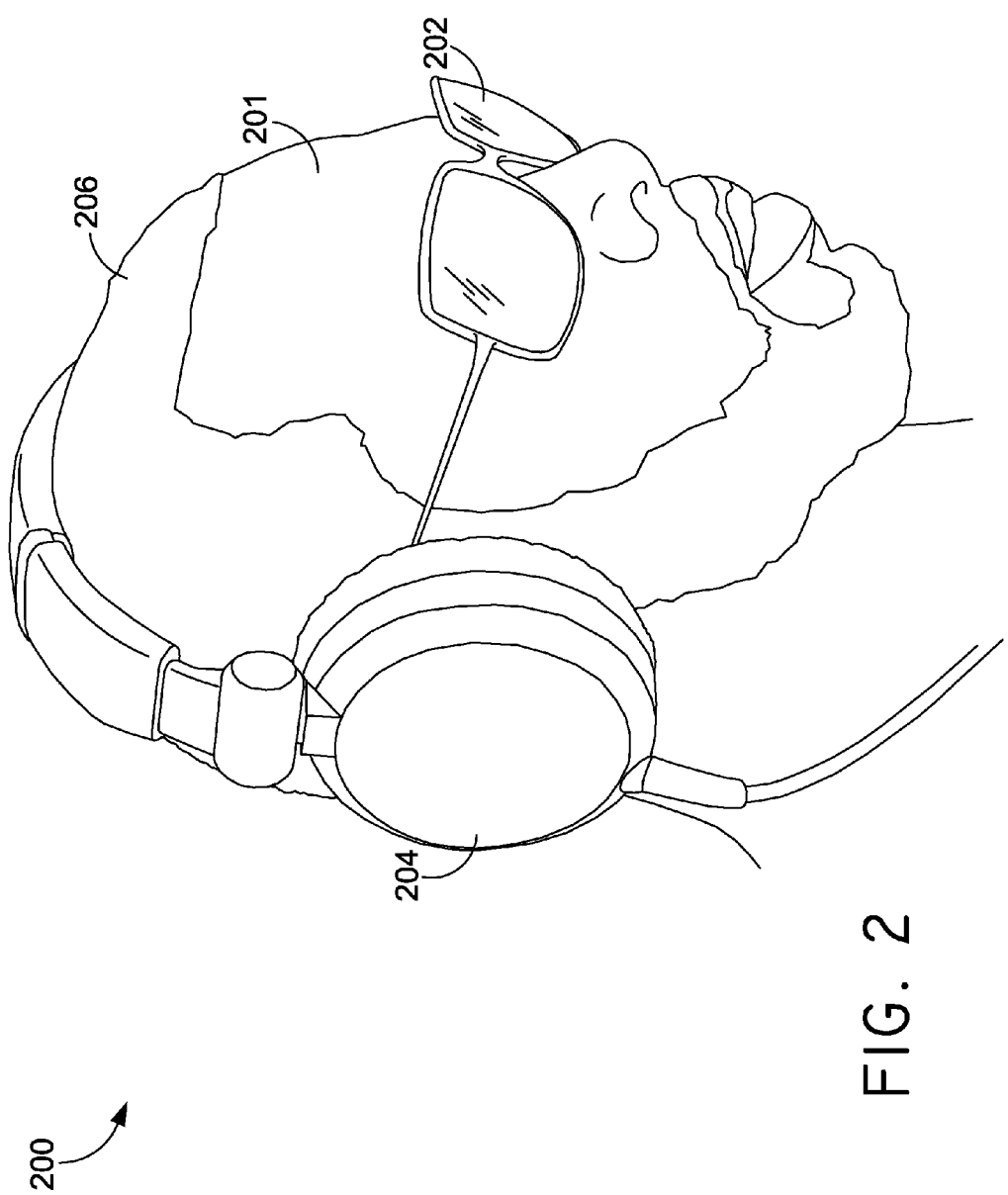
FIG. 2 illustrates another representative example of a multi-sensory training system, in accordance with aspect of the present invention.

FIG. 2 depicts another exemplary sensory manipulation system 200, in accordance with aspects of the present invention. The sensory manipulation system 200 provides a visual sensory manipulation component 202 and a pair of audio sensory manipulation components 204 and 206 positioned on a potential user 201. The sensory manipulation system 200 manipulates both visual and audible sensory inputs as perceived by the user 201

The visual sensory manipulation component 202 may be a strobe eyewear capable of variably adjusting spectral transmittance to obscure one or more portions of a visual field for the user 201. For example, it is contemplated that the visual sensory manipulation component 202 is an active shutter LCD lens that is able to transition between at least two states, a primarily transparent state and a primarily obscuring state, in response to one or more controls by a controller.

The of audio sensory manipulation components 204 and 206 may be either an active or passive audio vitiation devices. In this exemplary aspect, the audio sensory manipulation components 204 and 206 are exterior adapting earbuds capable of contacting the pinna portion of a user's ears. It is contemplated that each of the of audio sensory manipulation components 204 and 206 provide a speaker for generating a sound wave for utilization as an active solution or as an auditory input. Similarly, it is contemplated that each of the audio sensory manipulation components 204 and 206 may be comprised of one or more adjustable baffles or muffling technologies to passively vitiate audio inputs as perceived by the user 201.

Figure 3:
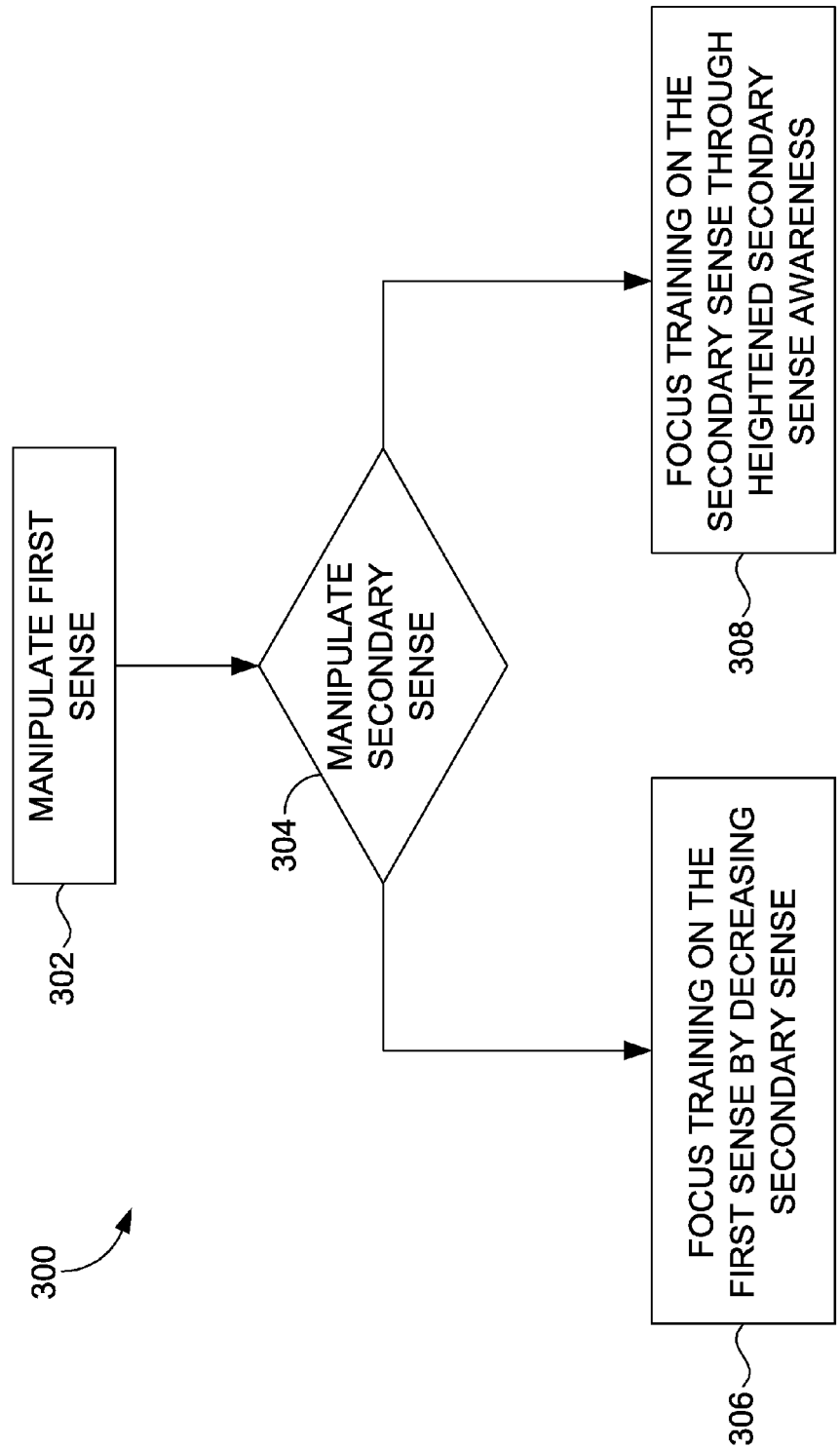
FIG. 3 illustrates an exemplary method of focusing training on one or more senses in a multi-sensory training environment, in accordance with aspects of the present invention.

FIG. 3 depicts an exemplary flow diagram for a method 300 of manipulating multiple senses to train one or more of the senses. For example, the method 300 begins with manipulating a first sense, as depicted in a block 302. The first sense may be any sense contemplated herein. In an exemplary aspect, the first sense to be manipulated at the block 302 is a visual sense. Vision may account for a substantial percentage of all inputs relied upon by a user when reacting to a situation. Consequently, in this exemplary aspect, manipulating the visual senses of a user may be a primary task. The manipulation of a sense may include reducing input typically provided by the environment. In the visual area, this may include obscuring at least a portion of a user's field of vision to prevent the user from obtaining information from the environment. For example, strobe eyewear may be used to obscure the vision of the user in a cyclical or constant manner.

At a block 304, a determination is made if a secondary sense is to be manipulated to further focus training on the first sense or if the secondary sense is to be manipulated to focus training on the secondary sense.

People may tend to compensate for a reduced sensory input by heightening an awareness of one or more senses. For example, when visual input is reduced for a user, the user may dedicate additional cognitive resources to other senses, such as hearing. A real-world example may be described by a person entering a dark room that inhibits their ability to see the contents of the room. As a result, some people may actually close their eyes (even though they are already unable to see anything) to focus their ability to hear, which is intended to aid in identifying potential threats in the dark space. However, the person is unable to control multiple sensory inputs in a controlled and prescribed manner as discussed herein. Additionally, levels of vitiation are not provided by the above example.

Therefore, if an input for a secondary sense (e.g., hearing) is vitiated to reduce that sense as a crutch to the primary sense, additional cognitive resources may be dedicated to the primary sense and the resulting training of that sense. As depicted in a block 306, training of the first sense may be enhanced by decreasing a secondary sense.

In an exemplary aspect, at the block 306 an audible input typically provided to a user is vitiated. For example, an active and/or a passive audio vitiation device may be employed to reduce the environmental noise perceived by the user. In an additional example, an audio vitiation device may continuously vitiate environmental noise input, which may force the user to dedicate additional resources to other senses, such as the first sense.

However, if at the block 304 a determination is made that a secondary sense should be focused on for training, at a block 308 the training is focused on the secondary sense through heightened secondary sense awareness. In an exemplary aspect, vitiating sensory input of the first sense may focus the user's attention towards at least the secondary sense. Returning to the dark room example, to focus training on hearing, the user may close their eyes to effectively reduce their visual input. Unlike the dark room example, a sensory manipulation system may be able to coordinate the manipulation of multiple senses and adjust the levels of manipulation based on desired levels of training.

A sensory manipulation system is contemplated as being able to manipulate a first sense to focus training on a secondary sense. Conversely, a sensory manipulation system is contemplated as being able to manipulate a second sense so that the first sense may be trained with manipulation. Further, it is contemplated the primary sense and the secondary sense may be trained contemporaneously through the manipulation of the both the primary and the secondary senses.

Figure 4:
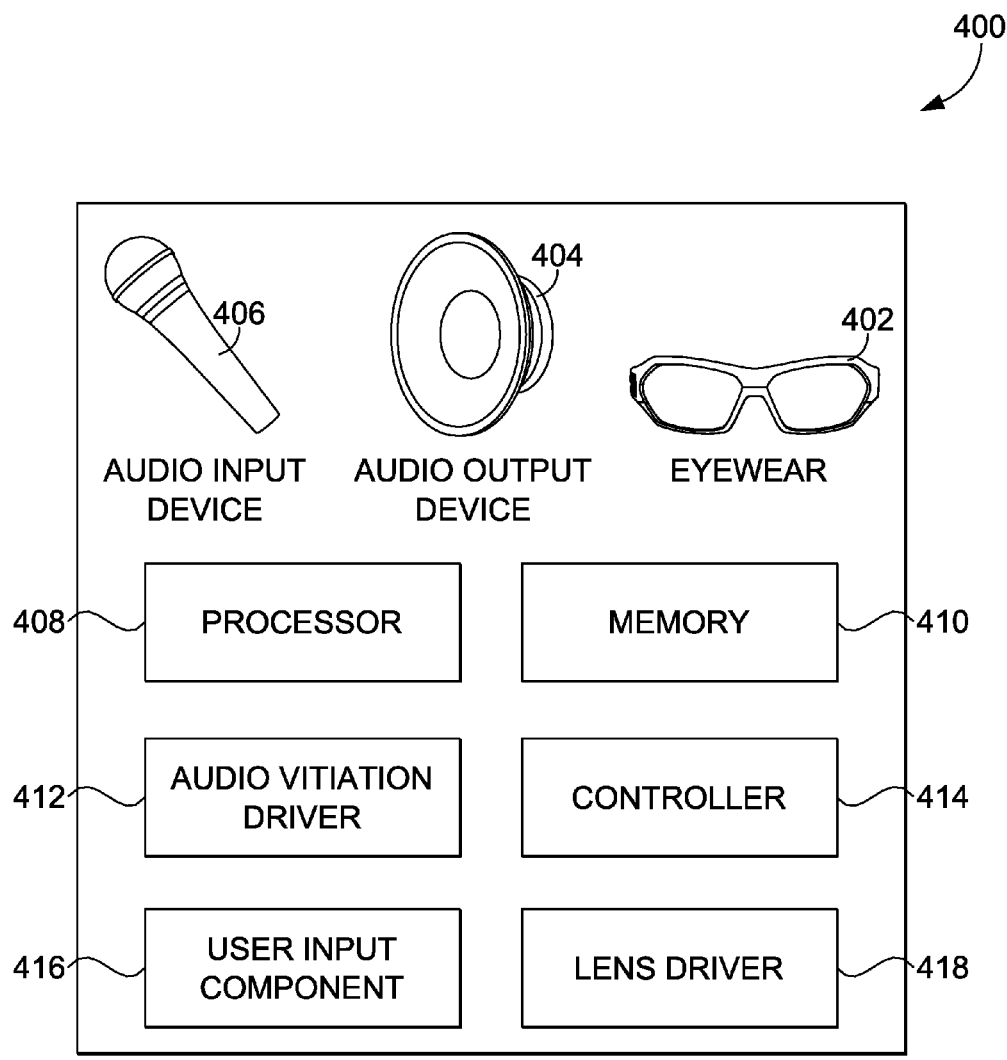
FIG. 4 illustrates an exemplary multi-sensory manipulation environment, in accordance with aspects of the present invention.

FIG. 4 depicts an exemplary environment 400 for operating a sensory manipulation system, in accordance with aspects of the invention. The sensory manipulation system may be comprised of eyewear 402, an audio output device 404, an audio input device 406, a processor 408, memory 410, an audio vitiation driver 412, a controller 414, a user input component 416, and a lens driver 418. The sensory manipulation system may have additional components/devices, fewer components/devices, and/or different quantities of components/devices in any combination.

While the exemplary sensory manipulation system of FIG. 4 is geared towards manipulating audio and visual inputs, it is contemplated that additional drivers and devices may be implemented for additional/different senses. For example, it is contemplated that a scent generator that releases prescribed scents may be coupled with an olfactory driver to effectuate the dispersement of the scents. Further it is contemplated that a tilt platform is couple with a balance driver to manipulate the sense of balance. Further, it is contemplated that a video device (as part of the eyewear 402 or as a standalone display) may be couple with a vertigo-balance driver to generate visual images that cause a disorientation and eventual balance disruption. Further, it is contemplated that a flavor generator is couple to a taste driver to generate a dispersement of flavor agents to manipulate the sense of taste. Also, it is contemplated that a pressure-generating article of clothing/wear is couple to a pain driver to generate a manipulation of tactile/pain feelings. It is contemplated that additional devices and drivers may be incorporated in any combination to allow for the manipulation of one or more senses.

Returning to FIG. 4, the eyewear 402 may be a strobe eyewear as previously discussed. In general, the eyewear 402 is useable to manipulate a visual input as perceived by a user. Stated differently, the eyewear 402 vitiates light waves to affect a sensory response of a user of the eyewear. While a traditional styled pair of glasses is depicted, it is understood that the eyewear may be goggles, a visor, contact lenses, or the like. As previously discussed, the eyewear 402, in an exemplary aspect, is described in detail in the co-pending U.S. Non-provisional patent application having an application Ser. No. 13/009,417, entitled Adjustable Spectral Transmittance Eyewear, filed Jan. 19, 2011, as was previously expressly incorporated by reference herein.

The audio output device 404 is a device for outputting audio information. For example, the audio output device 404 may be a speaker or other sound generating device. In an exemplary aspect, the audio output device 404 is in a near range to a user's ear, such as in earbuds. In an additional exemplary aspect, the audio output device 404 is remote from the user(s) such that it is typically larger and requires more power than a similar device in close proximity to the user.

The audio input device 406 is a device for receiving an audio input. For example, the audio input device 406 may receive audio information (e.g., sound waves) of the environmental noise. This audio input may then be used to generate, at least in part, to generate an anti-phased noise, a white noise, or other audio output from the audio output device 404 that may be used to vitiate the environmental noise(s). In an exemplary aspect, the audio input device 406 is a microphone-type device that is able to convert sound waves to an electrical signal. In other exemplary aspects, the audio input device 406 may be a mechanical device that concentrates or otherwise focuses the environmental noise(s), such as a stethoscope-type device. Therefore, the audio input device 406 and/or the audio output device 404 may be mechanical and/or electrical in nature.

The exemplary environment 400 typically includes a variety of computer-readable media. By way of example, and not limitation, computer-readable media may comprise Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices, or any other medium that can be used to encode desired information and be accessed by exemplary environment 400.

Memory 410 may be non-transitory computer-storage media in the form of volatile and/or nonvolatile memory. The memory may be removable, non-removable, or a combination thereof. Exemplary hardware devices include solid-state memory, hard drives, optical-disc drives, etc. Additionally, the exemplary environment 400 includes one or more processors 408 that read data from various entities such as memory 410, the controller 414, or the audio input device 406.

The audio vitiation driver 412 is an audio vitiation driver. In an active vitiation mode, the audio vitiation driver 412 generates one or more audio signals to be converted to an audible output by the audio output device 404. For example, the audio vitiation driver 412 may be responsible for generating a proper anti-phase sound signal based on one or more inputs from the audio input device 406.

The audio vitiation driver 412, in a passive vitiation mode, may be responsible for controlling an amount of muffling or dampening that is provided by the audio output device 404. For example, the audio output device 404 may include one or more baffles that are selectably adjusted for controlling an amount of sound energy that is transferred from the environment to a user's inner ear. The audio vitiation driver 412 may control the vitiation of environmental noise through controlling the transfer of sound energy.

Further, it is contemplated that the audio vitiation driver 412 may control both passive and active vitiation mechanisms. For example, both a passive audio vitiation system and an active audio vitiation system may be implemented, in combination, to effectively manipulate audio sensory inputs to a user.

The lens driver 418 is a driver of the electrically variable spectral transmittance of an exemplary eyewear 402. For example, one or more lenses of the eyewear 402 may transition from a first visual state to a second visual state, which is driven by the lens driver 418 in an exemplary aspect. Therefore, the driving of the lens from a first state to a second state may be implemented by the lens driver 418. In an exemplary aspect, a lens with variable spectral transmittance may have a plurality of potential spectral transmittance states, which may be controlled by the lens driver 418 by specifying a voltage or current to be applied to the lens.

The controller 414 is a component that coordinates the manipulation of two or more senses. For example, the controller 414 may coordinate the audio vitiation driver 412 and the lens driver 418 to provide multi-sensory manipulation training. The controller 414 may facilitate multi-sensory manipulation through a pre-programmed series of functions for each of the senses to be manipulated. Or, the controller 414 may allow for a user (or another person, such as a coach, trainer, and/or training partner) to provide an input that individually, or in combination, controls the senses to be manipulated. Different forms of sensory manipulation factors (e.g., duration, duty cycle, frequency intensity, in-phase, out-of-phase, and the like) that may be adjusted to achieve a desired level of multisensory manipulation will be discussed hereinafter.

In an exemplary aspect, the ability to coordinate controlling of at least two sensory manipulation devices (e.g., visual and audible) allows for a strategic and calculated training regime that allows various factors to be simultaneously and intentionally manipulated in coordination that would not be available otherwise. For example, when a user desires to train their hearing senses alone, the controller 414 may instruct the lens driver 418 to obscure the user's vision, by way of the eyewear 402, while various factors of an audible input are manipulated. However, the controller 414 may automatically instruct the lens driver 418 to manipulate the eyewear 402 at precise times to either initiate training, finalize training, or provide other visual cues as part of the training (e.g., strobing the eyewear 402 to provide an indication of selected level). In an additional aspect, the controller 414 may accurately and automatically control the audio vitiation driver to vitiate environmental noises to focus training on visual inputs as manipulated, at least in part, by the lens driver 418, which is also being controlled by the controller 414. Further yet, it is contemplated that the controller 414 controls both the audio vitiation driver (or any other sensory manipulation driver) and the lens driver 418 to provide a multi-sensory dynamic training experience. Therefore, the controller 414 is critical, in an exemplary aspect, at coordinating multiple sensory manipulation devices (or drivers) to allow for the simultaneous manipulation of two or more senses according to a predefined training regimen.

The user input component 416 is a component for receiving a user's (e.g. person whose senses are to be manipulated, a trainer, a coach, an instructor, or other third party) input for controlling at least a portion of a multi-sensory manipulation. For example, one or more predefined levels of sensory manipulation may be selected by a user. The level defines how features of a sensory input may be manipulated and may even define how multiple sensory manipulations are to be coordinated. Additionally, it is contemplated that a plurality of sensory manipulation systems may be controlled or used in conjunction with one another. For example, a group of athletes may train similar or different senses simultaneously utilizing similar or different manipulation patterns, which are controlled by a common source. Continuing with this example, a trainer may provide an input that controls two or more sensory manipulation systems used by two or more users at a common time (e.g., two baseball players playing catch with one another). The trainer in this example may cause an input to be communicated to each of the sensory manipulation devices, which then receive the input by way of the user input component 416 at each of the respective devices, in an exemplary aspect.

The user input component 416 may receive the user input by way of one or more physical buttons, radio signal, infrared signal, or other wired and/or wireless input options. For example, a combination of inputs is contemplated. An athlete may manipulate one or more buttons to provide a first user input while a third party (e.g., coach) utilizes a wireless transmitter to adjust or change the sensory manipulation being experienced by the athlete. This allows for the athlete, in this example, to initiate the sensory manipulation while allowing the coach to focus training on one or more senses and/or one or more features of a sense during the training exercise.

Figure 5:
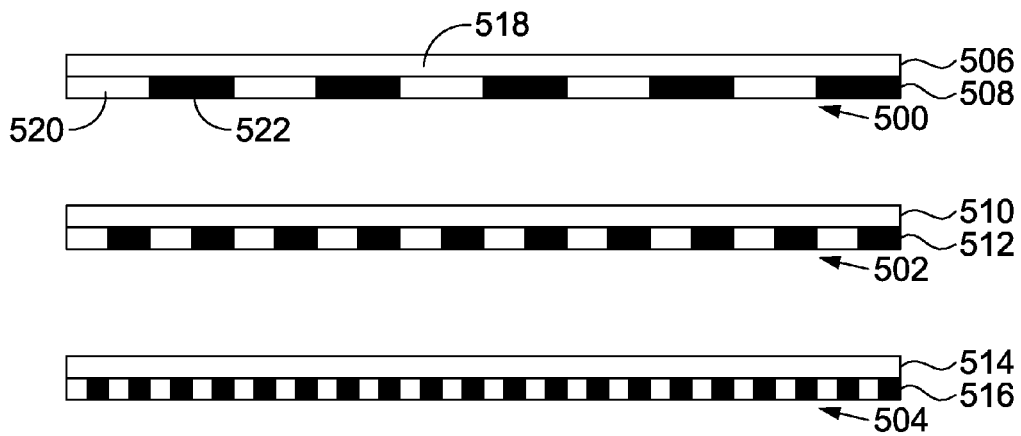
FIG. 5 illustrates an exemplary plurality of training levels having varied cycles for multiple sensory training, in accordance with aspects of the present invention.

FIG. 5 depicts a graphical representation of three levels of coordinated multi-sensory manipulations, in accordance with aspects of the present invention. The first level 500 depicts a first sensory manipulation pattern 506 for a first sense and a second sensory manipulation pattern 508 for a second sense. The first sensory manipulation pattern 506 is maintained in a first state 518. The second sensory manipulation pattern 508 is cycled from a first state 520 to a second state 522. In an exemplary aspect, the first sensory manipulation pattern 506 may represent a visual sense as manipulated by the eyewear 402 of FIG. 4. The first state 518 may therefore represent an obscured spectral transmittance state for one or more lenses of the eyewear 402. The second sensory manipulation pattern 508 may, in this exemplary aspect, represent an audible sense as being vitiated by the audio output device 404 of FIG. 4. The first state 520 may represent a minimally unencumbered environmental noise state and the second state 522 may represent a vitiated environmental noise state. Consequently, when interpreted from left to right, the first sensory manipulation pattern 506 maintains the first state 518 while the second sensory manipulation pattern 508 cycles from the first state 520 to the second state 522.

A second level 502 also depicts a first sensory manipulation pattern 510 and a second sensory manipulation pattern 512, where the first sensory manipulation pattern 510 maintains a first state. However, the second sensory manipulation pattern 512 cycles at a higher frequency from a first state to a second state than previously in the first level 500. A third level 504 also illustrates the coordinated cycling of two senses, a first sensory manipulation pattern 514 and a second sensory manipulation pattern 516. However, the second sensory manipulation pattern 516 has an even higher cycle frequency than in the second level 502 and the first level 500.

The progression from the first level 500 through the second level 502 to the third level 504 exemplifies the ability to selectively manipulate at least one feature for at least one sense. In this example, a frequency is increased for one sense while maintaining the frequency for the other sense. Additionally, this progression exemplifies that certain features may be maintained while manipulating other features for at least one sense (e.g., the duty cycles for the first sense and the second sense remain constant while manipulating the frequency of the secondary sense).

It is understood that the first level 500, the second level 502, and the third level 504 are merely exemplary in nature. It is contemplated that additional levels may be implemented in any combination, order, or sensory feature manipulation. Additionally, any sensory input may be represented by one or more of the sensory manipulation patterns (e.g., visual, audible, taste, olfactory, etc.). Further, it is contemplated that any number of states in any pattern for any sensory input may be manipulated in any of the discussed or implied manners to achieve a coordinated multi-sensory manipulation.

Figure 6:
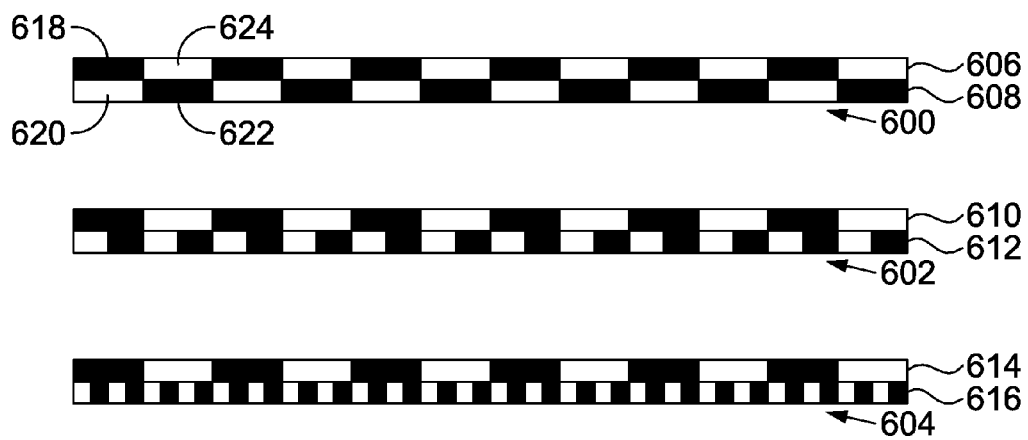
FIG. 6 illustrates another exemplary plurality of training levels having varied cycles for multiple sensory training, in accordance with aspects of the present invention.

FIG. 6 depicts a graphical representation of three additional levels of coordinated multi-sensory manipulation, in accordance with aspects of the present invention. A first level 600 illustrates a first sensory manipulation pattern 606 for a first sense having a first state 618 and a second state 624. The first level 600 also illustrates a second sensory manipulation pattern 608 for a second sense having a first state 620 and a second state 622. In an exemplary aspect, the first state 618 vitiates a sensory input for the first sense while the first state 620 does not substantially vitiate a sensory input of the second sense. Therefore, the first level 600 depicts an out-of-phase sensory manipulation of the first sense and the second sense.

A second level 602 illustrates a first sensory manipulation pattern 610 for the first sense and a second sensory manipulation pattern 612 for the second sense. However, the second sensory manipulation pattern 612 differs from the second sensory manipulation pattern 608 of the first level 600 as having a higher cycle frequency. Additionally, the first sensory manipulation pattern 610 and the second sensory manipulation pattern 612 alternate from out-of-phase to in-phase based on the coordinated, but different cycle frequency. A third level 604 includes a first sensory manipulation pattern 614 and a second sensory manipulation pattern 616. Again, the cycle frequency of the second sensory manipulation has increased from the second level 602 to the third level 604, while the first sensory manipulation pattern has remained constant, in this exemplary aspect.

The coordinated timing, frequency, duty cycle, duration, and other factors of a multi-sensory manipulation are possible, in an exemplary aspect, through the use of a controller, such as the controller 414 of FIG. 4. Without a controller in an exemplary aspect, introducing unintentional offsets of state changes between various senses may cause undesired affects on sensory training. For example, if visual stimulus is manipulated out of coordination with other sensory input, the user may experience a sense of vertigo or other distracting consequences that detract from the training at hand.

It is understood that the first level 600, the second level 602, and the third level 604 are merely exemplary in nature. It is contemplated that additional levels may be implemented in any combination, order, or sensory feature manipulation. Additionally, any sensory input may be represented by one or more of the sensory manipulation patterns (e.g., visual, audible, taste, olfactory, etc.). Further, it is contemplated that any number of states in any pattern for any sensory input may be manipulated in any of the discussed or implied manners to achieve a coordinated multi-sensory manipulation.

Figure 7:
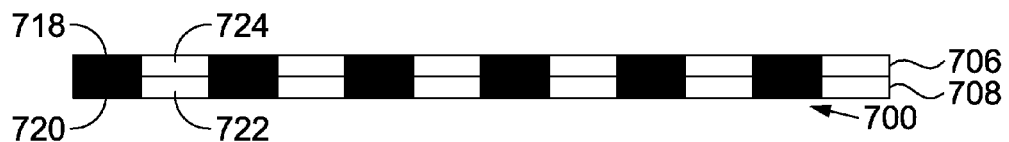
FIG. 7 illustrates another exemplary training level having in-phase cycles for multiple sensory training, in accordance with aspects of the present invention.

FIG. 7 depicts a graphical representation of an additional level 700 of a coordinated multi-sensory manipulation, in accordance with aspects of the present invention. The level 700 depicts a first sensory manipulation pattern 706 that cycles from a first state 718 of a first sense to a second state 724 of the first sense. Additionally, the level 700 also depicts a second sensory manipulation pattern 708 that cycles from a first state 720 of a second sense through a second state 722 of the second sense. The level 700 illustrates an exemplary in-phase multi-sensory manipulation. In this example, both the first sensory input and the second sensory input are manipulated at a common frequency for a common duration resulting in a common duty cycle. However, it is contemplated that the first sensory manipulation pattern 706 or the second sensory manipulation pattern 708 may deviate from a common feature value to provide a desired offset (e.g., introduction of an out-of-phase sensory manipulation).

Figure 8:
FIG. 8 illustrates a first state and a second state duration corresponding to an exemplary repetitive cycle, in accordance with aspects of the present invention.
Figure 9:
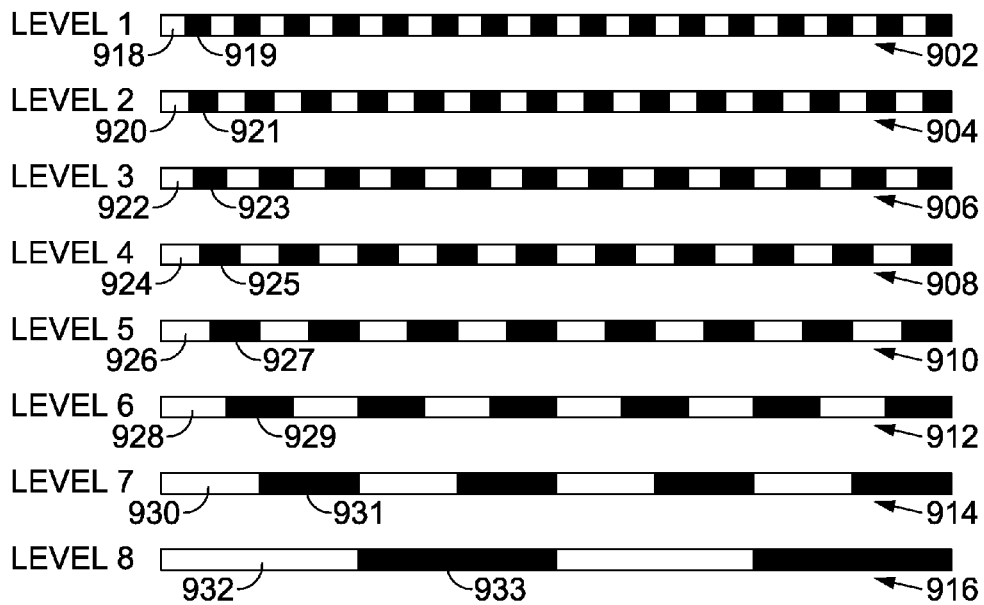
FIG. 9 illustrates another first state and a second state exemplary repetitive cycle having a constant duty cycle and a varied frequency with each level, in accordance with aspects of the present invention.
Figure 10:
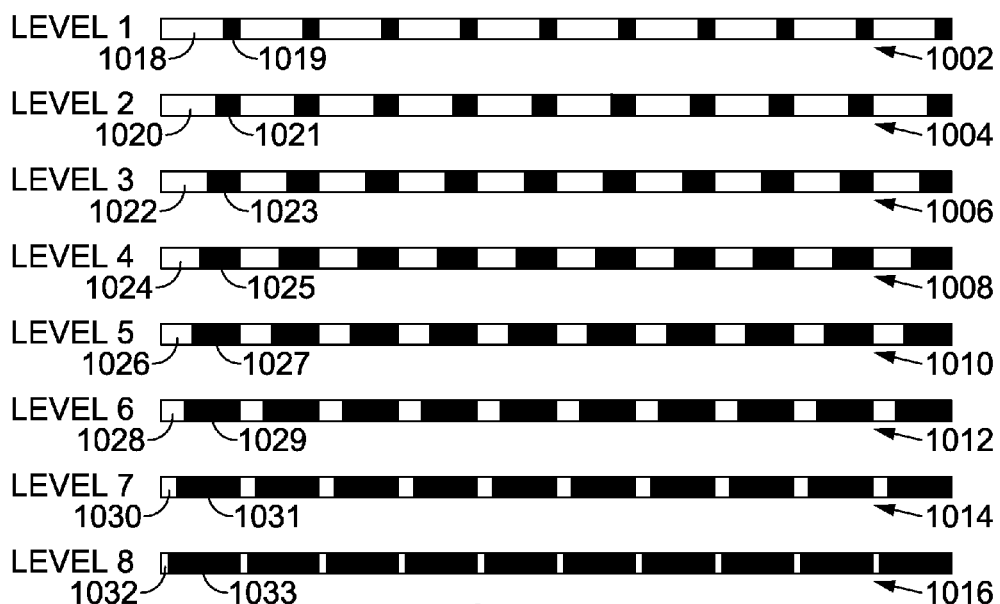
FIG. 10 illustrates a first state and a second state exemplary repetitive cycle having a varied duty cycle and a constant frequency with each level, in accordance with aspects of the present invention.

The following FIGS. 8-10 illustrate exemplary sensory manipulation patterns for various levels for a single sense, in accordance with aspect of the present invention. It is contemplated that any exemplary level may be coordinated with any other (or the same) exemplary level for one or more additional senses. For example, it is contemplated that a first level 802 of FIG. 8 may apply to a first sense while an eighth level 1016 of FIG. 10 may be applied to a second sense in a coordinated multi-sensory manipulation. As such, any combination of exemplary sensory manipulation patterns may be used in conjunction with one another to achieve a desired multi-sensory manipulation.

Various levels of sensory manipulation may be achieved through the manipulation of one or more variables. For example, a duration, duty cycle, intensity, vitiation percentage/level, and/or frequency may be manipulated for a single sensory input. When additional sensory inputs are also manipulated in coordination, in-phase, out-of-phase, timing, and other variables may also be manipulated. Further, directional sensory inputs (e.g., right eye/left eye, right ear/left ear, right tactile/left tactile) may also be manipulated independently, in coordination, in-phase, out-of phase, and other combination between one sense or a combination of senses. Consequently, pattern variability provides a substantial opportunity for diversified training regiments. Sensory manipulation may include further examples of directional manipulation. For example, audio input may be manipulated to create a directional variation in the horizontal direction (e.g., front, right, back, and/or left relative to a user) and in the vertical direction (e.g., above and/or below the user). Therefore, sensory input may be manipulated so as to manipulate a perceived location (e.g., origination) of the sensory input. In use, an example may include a soccer player that trains/tests audible sensory input that is manipulated left and right to achieve a better awareness of audible input when on the soccer field from other players providing call outs to the user.

Additionally, it is contemplated that different senses may utilize different manipulation patterns/levels. For example, training of a visual sense may allow for the vitiation of a significant portion of visual information (e.g., duration, frequency, intensity, and the like), while olfactory sensory training may only vitiate a minimal amount of olfactory input (e.g., duration, frequency, intensity, and the like). As indicated above, an amount of vitiation may also be adjusted by changing an intensity or input received during any given period. For example, in addition to, or in place of, manipulating a duration, frequency, and/or duty cycle of an input, a percentage of the input may also be manipulated. For example, instead of strobing a sensory input for 100% (e.g., transparent) to 0% (e.g., obscured), any intensity may be utilized. The ability to manipulate an intensity may be useful in the training of senses that typically perceive intensity (e.g., loud versus quite sounds, strong versus faint smells).

The following is a table showing a relationship between duty cycle, frequency, and level when one of the potential states of a sensory input is remains constant for a repetitive sequence of first state/second state intervals.

| Level | First State (Sec.) | Duty Cycle (%) | Frequency (Hz) |
|---|---|---|---|
| 1 (easiest) | 0.025 | 20 | 8 |
| 2 | 0.043 | 30 | 7 |
| 3 | 0.067 | 40 | 6 |
| 4 | 0.1 | 50 | 5 |
| 5 | 0.15 | 60 | 4 |
| 6 | 0.233 | 70 | 3 |
| 7 | 0.4 | 80 | 2 |
| 8 (hardest) | 0.9 | 90 | 1 |

FIG. 8 illustrates a first (e.g., less attenuated, less vitiated) state and a second (e.g., more attenuated, more vitiated) state duration corresponding to the above-provided table, in accordance with aspects of the present invention. The representative arrangement of eight levels of difficulty represented by FIG. 8 includes durations of the first state intervals and the second state intervals for an "easiest" level 802, a "hardest" level 816, and intermediate levels 804, 806, 808, 810, and 812 are shown. In the exemplary levels of FIG. 8, first state intervals 818, 820, 822, 824, 828, 830, and 832 have a fixed duration of 0.1 sec, while second state intervals 819, 821, 823, 825, 827, 829, 831, and 833 have durations that increase with increasing level of difficulty. For example, the most difficult level, 816, provides a 0.9 sec interval of second state during which the user's sensory input for a particular sense is obscured/vitiated. For all the levels of FIG. 8, a repetitive sequence of first state/second state intervals are provided and first state/second state intervals for a representative 1 second time period are shown. As previously discussed with the above table, maintaining a constant duration for a single state may cause both a frequency and a duty cycle to change when also changing a duration for a second state of spectral transmittance.

Further, it is contemplated that a first state and a second state may maintain a common duty cycle (e.g., 50% second state/50% first state, 40% second state/60% first state, 60% second state/40% first state) but the frequency may be adjusted. For example, the following table utilizes an exemplary 50% duty cycle for a 1 second period the first state and the second state repetitive cycle. Therefore, a level of difficulty is adjusted by altering a frequency at which the cycle occurs. The following is an example and it is contemplated that other frequencies, duty cycles, and durations may be used.

| Level | First State (Sec.) | Duty Cycle (%) | Frequency (Hz) |
|---|---|---|---|
| 1 (easiest) | 0.5 | 50 | 16 |
| 2 | 0.5 | 50 | 14 |
| 3 | 0.5 | 50 | 12 |
| 4 | 0.5 | 50 | 10 |
| 5 | 0.5 | 50 | 8 |
| 6 | 0.5 | 50 | 6 |
| 7 | 0.5 | 50 | 4 |
| 8 (hardest) | 0.5 | 50 | 2 |

FIG. 9 illustrates a first (e.g., less attenuated, less vitiated) state having a fixed duty cycle and a second (e.g., more attenuated, more vitiated) state having a fixed duty cycle corresponding to the above-provided table, in accordance with aspects of the present invention. The representative arrangement of eight levels of difficulty represented by FIG. 9 include durations of the first state intervals and the second state intervals for an first level 902, an eighth level 916, and intermediate levels 904, 906, 908, 910, and 912 are shown. In the example levels of FIG. 9, first state intervals 918, 920, 922, 924, 928, 930, and 932 have a constant duty cycle, but their durations change with a change in frequency. Similarly, the second state intervals 919, 921, 923, 925, 927, 929, 931, and 933 have durations that increase with decreases in frequency, while maintaining a constant duty cycle. For all the levels of FIG. 9, a repetitive sequence of first state/second state intervals are provided and first state/second state intervals for a representative 1 second time period are shown.

Additionally, it is contemplated that a frequency may be maintained constant (e.g., 2 Hz, 5 Hz, 8 Hz, 12 Hz, 20 Hz) while adjusting the duty cycle for one of the sensory states (i.e., first state, second state, or mid-level state). The following table provides an exemplary aspect where a 10 Hz frequency (exemplary in nature) is maintained while adjusting a duty cycle for the first state. As previously indicated, this is but one exemplary arrangement of frequency, duty cycle, and/or duration that may be adjusted. Additional aspects are contemplated.

| Level | First State (Sec.) | Duty Cycle (%) | Frequency (Hz) |
|---|---|---|---|
| 1 (easiest) | 0.02 | 20 | 10 |
| 2 | 0.03 | 30 | 10 |
| 3 | 0.04 | 40 | 10 |
| 4 | 0.05 | 50 | 10 |
| 5 | 0.06 | 60 | 10 |
| 6 | 0.07 | 70 | 10 |
| 7 | 0.08 | 80 | 10 |
| 8 (hardest) | 0.09 | 90 | 10 |

FIG. 10 illustrates a first (e.g., less attenuated, less vitiated) state and second (e.g., more attenuated, more vitiated) state duration corresponding to the above-provided table, in accordance with aspects of the present invention. The representative arrangement of eight levels of difficulty represented by FIG. 10 include durations of first state intervals and second state intervals that maintain a constant frequency, but adjust a duty cycle to change a level of difficulty. For example, the levels of FIG. 10 include an "easiest" level 1002, a "hardest" level 1016, and intermediate levels 1004, 1006, 1008, 1010, and 1012 are shown. In the example levels of FIG. 10, a constant frequency of 10 Hz is represented (10 cycles per second) with a changing duty cycle for the second state (and as a result, also the first state). Consequently, the first state intervals 1018, 1020, 1022, 1024, 1028, 1030, and 1032 have a duration that decreases with an increase in the second state duty cycle. The second state intervals 1019, 1021, 1023, 1025, 1027, 1029, 1031, and 1033 have durations that increase with increases in the second state duty cycle. For all of the levels of FIG. 10, a repetitive sequence of first state/second state intervals are provided and first state/second state intervals for a representative 1 second time period are shown.

Additional exemplary scenarios may include selections from the following tables. It is understood that a first state and/or a second state may be any state provided herein. For example, the first state may be a transparent state (e.g., clear) and a second state may be an obscured states (e.g., opaque). Further it is contemplated that one or more state durations are modified for one or more additional aspects.

| Level | First State (Sec.) | Second State (Sec.) | Frequency (Hz) |
|---|---|---|---|
| 1 | 0.1 | 0.025 | 8 |
| 2 | 0.1 | 0.043 | 7 |
| 3 | 0.1 | 0.067 | 6 |
| 4 | 0.1 | 0.100 | 5 |
| 5 | 0.1 | 0.150 | 4 |
| 6 | 0.1 | 0.233 | 3 |
| 7 | 0.1 | 0.400 | 2 |
| 8 | 0.1 | 0.900 | 1 |

| Level | First State (Sec.) | Second State (Sec.) | Frequency (Hz) |
|---|---|---|---|
| 1 | 0.1 | 0.067 | 6 |
| 2 | 0.1 | 0.100 | 5 |
| 3 | 0.1 | 0.150 | 4 |
| 4 | 0.1 | 0.233 | 3 |
| 5 | 0.1 | 0.344 | 2.25 |
| 6 | 0.1 | 0.471 | 1.75 |
| 7 | 0.1 | 0.650 | 1.333 |
| 8 | 0.1 | 0.900 | 1 |

| Level | First State (Sec.) | Second State (Sec.) | Frequency (Hz) |
|---|---|---|---|
| 1 | 0.067 | 0.067 | 7.5 |
| 2 | 0.1 | 0.100 | 5 |
| 3 | 0.1 | 0.150 | 4 |
| 4 | 0.1 | 0.233 | 3 |
| 5 | 0.1 | 0.344 | 2.25 |
| 6 | 0.1 | 0.471 | 1.75 |
| 7 | 0.1 | 0.650 | 1.33 |
| 8 | 0.1 | 0.900 | 1 |

An exemplary scenario for utilizing a multi-sensory manipulation system may be in the athletic training field. For example, it is contemplated that an athlete may desire to train one or more senses, such as vision and hearing. When training the senses, the athlete may decide to focus on one of the senses in particular. To aid in focusing on a particular sense, it may be advantageous to vitiate one or more other senses to prevent the athlete from consciously, or subconsciously, heightening their awareness of the non-trained senses to compensate for the reduction of sensory input to the sense being trained. Therefore, in this example, the athlete may selectively vitiate the "crutch" senses to allow a focus on the trained sense.

However, it is also contemplated that two or more sense are trained concurrently utilizing a multi-sensory manipulation system. For example, two senses, either in phase or out of phase, are concurrently trained. An example may include obscuring a portion of an athlete's vision while also vitiating audio input(s). The resulting coordinated sensory input manipulation may allow an athlete to heighten their abilities to utilize a lesser amount of sensory input to facilitate making a determination, reaction, and/or decision.

Additionally, it is contemplated that a user, such as an athlete, may progress through a series of levels that train one or more senses through the predefined and coordinated manipulation of the senses. As such, it is contemplated that a user reduces a sensory input minimally until their ability to adapt to the minimized sensory input is increased. Once their ability to adapt improves, another sensory input may be manipulated and/or the original sensory input may be further manipulated. As such, a first sense may progress through a series of levels while a second sense also progresses through corresponding, complimentary, or independent levels.

Many different arrangements of the various components depicted, as well as components not shown, are possible without departing from the spirit and scope of the present invention. Aspects of the present invention have been described with the intent to be illustrative rather than restrictive. Alternative aspects will become apparent to those skilled in the art that do not depart from its scope. A skilled artisan may develop alternative means of implementing the aforementioned improvements without departing from the scope of the present invention.

In view of the many possible aspects to which the principles of the disclosed technology may be applied, it should be recognized that the illustrated aspects are only preferred examples and should not be taken as limiting the scope of the technology. Rather, the scope is defined by the following claims. We therefore claim all that comes within the scope and spirit of the appended claims.

The invention claimed is:

1. A sensory manipulation training system, comprising:
   an audio output device;
   an audio vitiation driver that generates audio information for output by the audio output device, wherein the audio information comprises a first audio state and a second audio state, wherein an environmental noise is more capable of being perceived by a user during the first audio state than during the second audio state, and wherein the audio information cycles between the first audio state and the second audio state at a frequency; and
   an audio vitiation controller that, in response to a sensory manipulation-level input received from the user, controls a duty cycle, a duration of the first audio state and/or the second audio state, or the frequency.

2. The system of claim 1, wherein the audio output device is a speaker.

3. The system of claim 1, wherein the audio information during the first audio state comprises a noise having a decibel greater than the environmental noise.

4. The system of claim 1, wherein the second audio state of the audio information is a passive state for the audio output device.

5. The system of claim 1, wherein the audio information during the second audio state is substantially similar to the environmental noise.

6. The system of claim 1, wherein a vitiation level of the environmental noise provided by the first audio state is adjustable by the sensory manipulation-level input.

7. The system of claim 1 further comprising an input device capable to provide an input, wherein the input is based, at least in part, on the environmental noise.

8. The system of claim 7, wherein the input is utilized by the audio vitiation driver to generate audio information state during the first state.

9. The system of claim 1, wherein the audio information comprises an anti-phased noise during the first audio state.

10. A sensory manipulation training system, comprising:
eyewear configured with electrically variable spectral transmittance;
an audio vitiation device configured to cycle a variable audio transmittance at a frequency; and
a controller configured to control the eyewear and the audio vitiation device such that the electrically variable spectral transmittance of the eyewear and the frequency of the variable audio state of the audio vitiation device are adjustable in response to a user input.

11. The system of claim 10, wherein the electrically variable spectral transmittance includes a first spectral transmittance state and a second spectral transmittance state, the first spectral transmittance state is more obscuring than the second spectral transmittance state.

12. The system of claim 10, wherein the variable audio transmittance is comprised of a first audio state and a second audio state, and wherein the first audio state vitiates an environmental noise more than the second audio state.

13. The system of claim 12, wherein the first audio state is achieved utilizing an electronic audio output device, wherein the first audio state and the second audio state each comprise a duration, and wherein the duration of the first audio state and/or the second audio state are adjustable in response to the user input.

14. The system of claim 12, wherein the first audio state is achieved utilizing an anti-phased noise, and wherein the variable audio transmittance further comprises a duty cycle that is adjustable in response to the user input.

15. The system of claim 10, wherein the variable audio transmittance is comprised of a first audio state and a second audio state, and wherein the first audio state occludes more of the environmental noise than the second audio state.

16. The system of claim 10, wherein the controller coordinates the electrically variable spectral transmittance and the variable audio transmittance in response to a common input.

17. The system of claim 10, wherein the controller controls the eyewear to increase an obscuring spectral transmittance state and the controller controls the audio vitiation device to increase an audio vitiation state.

18. The system of claim 10, wherein the controller controls the eyewear to decrease an obscuring spectral transmittance state and the controller controls the audio vitiation device to decrease an audio vitiation state.

19. The system of claim 10, wherein the controller controls the eyewear to increase an obscuring spectral transmittance state and the controller controls the audio vitiation device to decrease an audio vitiation state.

20. A sensory manipulation training system, comprising:
eyewear configured with electrically variable spectral transmittance that cycles between a first visual state and a second visual state, wherein the first visual state obscures more than the second visual state;
an audio vitiation device configured to cycle a variable audio transmittance between a first audio state and a second audio state at a frequency adjustable in response to a user input, wherein the audio transmittance is vitiated more during the first audio state than during the second audio state; and
a controller configured to control the eyewear and the audio vitiation device in response to the user input such that the first visual state and the first audio state are controlled contemporaneously.

* * * * *